(12) United States Patent
Ritchart

(10) Patent No.: US 6,605,096 B1
(45) Date of Patent: Aug. 12, 2003

(54) PERCUTANEOUS SUTURING APPARATUS AND METHOD

(75) Inventor: Mark A. Ritchart, Murrieta, CA (US)

(73) Assignee: Opus Medical, Inc, San Juan Capistrano, CA (US)

( * ) Notice: Subject to any disclaimer, the term of this patent is extended or adjusted under 35 U.S.C. 154(b) by 0 days.

(21) Appl. No.: 09/909,928

(22) Filed: Jul. 20, 2001

(51) Int. Cl.⁷ ............................................. A61B 17/04
(52) U.S. Cl. ....................... 606/144; 606/148; 606/205; 606/96
(58) Field of Search ................. 606/205, 139, 606/144, 147, 148, 211, 96

(56) References Cited

U.S. PATENT DOCUMENTS

| | | | |
|---|---|---|---|
| 919,138 A | 4/1909 | Drake et al. | |
| 2,286,578 A | * 6/1942 | Sauter | ........................ 606/148 |
| 3,946,740 A | 3/1976 | Bassett | |
| 4,345,601 A | 8/1982 | Fukuda | |
| 4,373,530 A | 2/1983 | Kilejian | |
| 4,621,640 A | 11/1986 | Mulhollan et al. | |
| 4,781,182 A | * 11/1988 | Purnell et al. | ................. 606/96 |
| 4,836,205 A | 6/1989 | Barrett | |
| 4,923,461 A | 5/1990 | Caspari et al. | |
| 4,935,027 A | 6/1990 | Yoon | |
| 4,957,498 A | 9/1990 | Caspari et al. | |
| 5,059,201 A | 10/1991 | Asnis | |
| 5,222,977 A | 6/1993 | Esser | |
| 5,312,422 A | 5/1994 | Trott | |
| 5,409,494 A | * 4/1995 | Morgan | ........................ 606/96 |
| 5,417,699 A | 5/1995 | Klein et al. | |
| 5,431,666 A | 7/1995 | Sauer et al. | |
| 5,454,823 A | * 10/1995 | Richardson et al. | ......... 606/148 |
| 5,522,820 A | * 6/1996 | Caspari et al. | ............... 606/148 |
| 5,573,542 A | 11/1996 | Stevens | |
| 5,575,801 A | * 11/1996 | Habermeyer et al. | ........ 606/148 |
| 5,618,290 A | 4/1997 | Toy et al. | |
| 5,792,152 A | 8/1998 | Klein et al. | |
| 5,860,991 A | 1/1999 | Klein et al. | |
| 5,904,692 A | 5/1999 | Steckel et al. | |
| 6,022,360 A | 2/2000 | Reimels et al. | |
| 6,143,004 A | 11/2000 | Davis et al. | |
| 6,217,592 B1 | 4/2001 | Freda et al. | |

FOREIGN PATENT DOCUMENTS

DE  25 32 242  7/1975

* cited by examiner

Primary Examiner—Julian W. Woo
(74) Attorney, Agent, or Firm—Stout, Uxa, Buyan & Mullins, LLP; Donald E. Stout

(57) ABSTRACT

A suturing instrument and methods for placing stitches in soft tissues combines the functions of both independently grasping the tissue and passing sutures through the tissue to form a mattress stitch therein. The endoscopic suturing instrument comprises a clamping portion having a longitudinal axis, which is adapted for percutaneous entry into an operative site. The clamping portion further comprises a plurality of jaw members that are movable relative to one another between a closed position wherein the jaw members are disposed in close proximity to one another and an open position wherein the jaw members are spaced apart. A needle portion is disposed at an angle relative to the longitudinal axis, and is adapted for percutaneous entry into said operative site. The needle portion comprises a needle, and preferably a pair of needles, for passage through a portion of soft tissue disposed between the jaw members of the clamping portion.

19 Claims, 4 Drawing Sheets

PERCUTANEOUS SUTURING APPARATUS AND METHOD

This application is related to Application Ser. No. 09/547,171, filed on Apr. 11, 2000, entitled *Dual Function Suturing Apparatus and Method*, and to Application Ser. No. 09/668,055, filed on Sep. 21, 2000, entitled *Linear Suturing Apparatus and Methods*, both of which are herein expressly incorporated by reference.

BACKGROUND OF THE INVENTION

The present invention relates to a method and apparatus for placing sutures in tissue, and more particularly to a method and device for arthroscopic repair of a torn rotator cuff.

Suturing of body tissues is a time consuming aspect of most surgical procedures. Many surgical procedures are currently being performed where it is necessary to make a large opening to expose an area of the body which requires surgical repair. There are instruments that are becoming increasingly available that allow the viewing of certain areas of the body through a small incision without exposing the entire body cavity. These viewing instruments, called endoscopes, can be used in conjunction with specialized surgical instrumentation to detect, diagnose, and repair areas of the body that were previously only able to be repaired using traditional "open" surgery.

In the past, there have been many attempts to simplify the surgeons' task of driving a needle-carrying suture through body tissues to approximate, ligate and fixate them. Many prior disclosures, such as described in U.S. Pat. No. 919,138 to Drake et al, employ a hollow needle driven through the tissue with the suture material passing through the hollow center lumen of the needle. The needle is withdrawn, leaving the suture material in place, and the suture is tied, completing the approximation. A limitation of these types of devices is that they are particularly adapted for use in open surgical procedures, involving a large incision, where there is room for the surgeon to manipulate the instrument.

Others have attempted to devise suturing instruments that resemble traditional forceps, such as U.S. Pat. No. 3,946,740 to Bassett. These devices pinch tissue between opposing jaws and pass a needle from one jaw through the tissue to the other jaw, where grasping means pull the needle and suture material through the tissue. A limitation of these designs is that they also are adapted primarily for open surgery, in that they require exposure of the tissues to be sutured in order that the tissue may be grasped or pinched between the jaws of the instrument. This is a severe limitation in the case of endoscopic surgery.

The term "endosurgery" means endoscopic surgery or surgery performed using an endoscope. In conjunction with a video monitor, the endoscope becomes the surgeons' substitute eyes by which they operate. Operations using an endoscope are significantly less invasive when compared to traditional open surgery. Patients usually return home the next day or in some cases, the same day of the endosurgical procedure. This is in contrast to standard open surgical procedures where a large incision divides the muscle layers and allows the surgeon to directly visualize the operative area. Patients may stay in the hospital for 5 to 6 days or longer following open surgery. In addition, after endosurgical procedures, patients return to work within a few days versus the traditional 3 to 4 weeks at home following open surgery.

It should be noted that different surgical specialties have more specific names for endoscopes that have been adapted for their primary use. General and Gynecologic surgeons call theirs laparoscopes, Cardiovascular surgeons call theirs thorascopes, Orthopedic surgeons use arthroscopes. All of these and others are included under the general heading of endoscopes.

Access to the operative site using endosurgical or minimally invasive techniques is accomplished by inserting small tubes called trocars into a body cavity. These tubes have a diameter of, for example, between 3 mm and 30 mm and a length of about 150 mm (6 inches). There have been attempts to devise instruments and methods for suturing within a body cavity through these trocar tubes.

Such an instrument is disclosed in U.S. Pat. No. 4,621,640 to Mulhollan et al. The Mulhollan et al. patent describes an instrument that may be used to hold and drive a needle, but makes no provision for retrieval of the needle from the body cavity, nor the completion of the suture by tying. Mulhollan's instrument is limited in that the arc through which the needle must be driven is perpendicular to the axis of the device.

Another such instrument intended for endoscopic use is described by U.S. Pat. No. 4,935,027 to Yoon. This instrument uses oppositional hollow needles or tracks pushed through the tissue and coapted to create a tract through which the suture material is pushed. It is not clear how the curved tracks would be adapted to both be able to pierce the tissue planes illustrated, parallel to the tips of the tracks, and be curved toward each other to form the hollow tract.

Yet another instrument and method is shown by Caspari in U.S. Pat. Nos. 4,923,461 and 4,957,498. Caspari discloses an endoscopic instrument suitable for use through a trocar that resembles the Yoon approach, but with a single hollow needle on one of a set of oppositional jaws. The jaws simultaneously close, grasping the tissue. The jaw opposite the hollow needle has a window through which the hollow needle passes as the jaws close, freeing the lumen of the hollow needle from the tissue. Much like Yoon, a suture snare or relatively stiff monofilament suture which is not appropriate for many procedures is pushed down through the lumen and retrieved from the suture site, the jaws are released, and the suture is pulled back out through the trocar. This device may be used to place simple stitches in tissues that have been mobilized and have an edge accessible to the jaws. A limitation of the device is the manipulation that must be done with the snare if a suture other than a monofilament is used or a stitch other than a simple stitch is desired.

Another instrument specifically adapted for the orthopedic surgeon for the repair of a torn anterior cruciate ligament or for meniscal repair is disclosed by U.S. Pat. No. 4,836,205 to Barrett. The Barrett patent combines in a single instrument the functions of grasping the tissue to be sutured and the passing of the needles through that tissue. It is to be understood that this instrument is designed for use specifically under endoscopic view, and through trocars as previously described. A fairly generic endoscopic grasper is disclosed that has been adapted to allow for a hollow lumen from the handle of the grasper down to the distal tip of the grasper jaws. An elongate needle of 8 to 10 inches in length may be passed through this hollow lumen. The needle, being significantly longer than the grasper, is introduced through the handle of the grasper, and may be driven through the tissue being held in the grasping jaws of the device. The needle is then retrieved from the tissue via a trocar port placed substantially opposite the port through which the grasper is introduced. If a mattress stitch is desired, two needles attached to opposite ends of a suture are both passed through the tissue and retrieved. A limitation of this device is that there must be both visual and physical access to both sides of the tissue flap to be sutured. This requires trocars to be placed opposite each other and roughly on a line intercepting the tissue. This is a severe limitation in the instance of shoulder repair or in any procedure that requires suturing down and into a blind hole, and specifically in repair of the rotator cuff.

Yet another instrument adapted for use with the aid of an arthroscope is described in U.S. Pat. No. 5,059,201 issued to Asnis. This patent discloses an elongate instrument adapted for threading a loop of suture through a piece of tissue. The instrument includes an extractor shaft assembly which is slidably disposed within an outer tube. The extractor has a pointed front end adapted for tissue penetration, and a hook directly behind the front end adapted for retrieval of the suture loop. The outer tube is moveable proximal to distal to clamp tissue between itself and a bracket disposed at the distal end of the instrument. This bracket also holds the suture loop. In practice, the suture is secured to the bracket at a point mid-length, and the ends of the suture are tied or otherwise joined together. The instrument is introduced into the surgical site, either directly into the wound or through a trocar, and the tissue to be sutured is clamped between the outer tube and the distal bracket. The extractor is pushed through the clamped tissue, engages the loop of suture with the hook, and the suture is withdrawn back through the tissue, pulling the loop proximally back through loop formed by the joined ends, creating a slip knot around the piece of tissue grasped. This is not the preferred method of securing suture to tissue for shoulder repair as the suture would tend to garrot or strangulate the tendon within the loop.

Another instrument adapted for endoscopic use is disclosed in U.S. Pat. No. 5,431,666 issued to Sauer et al. and describes an instrument with an elongated body assembly with a mechanism adapted to sequentially pull the ends of a suture coupled to ferrules through tissue by coupling the ferrules with needles driven through the tissue. This instrument does not have the capacity to clamp or otherwise immobilize the tissues to be sutured. This limitation requires additional manipulation of the instrument to properly locate the tissue to be sutured in the throat of the instrument, as well as making it difficult to secure a good bite of tissue when suturing.

There have been other attempts to improve the methods of tissue repair. These include the development of staplers and anchoring devices. In response to some of the aforementioned problems in placing sutures in tissues endoscopically, manufacturers have developed tissue staplers. These devices utilize stainless steel or titanium staples that are constructed much like the staples used to hold papers together. The major disadvantage of these kinds of staplers is that they leave metal in the body. For some tissues this is not a problem, however in some procedures, metal staples left within the tissues can be a major hindrance to the healing process.

In orthopedic surgery, many different designs for bone anchors have been developed. These anchors allow soft tissues to be reattached to bone, and simplify the process by removing the need to create a trans-osseous tunnel. Trans-osseous tunnels are created in bones to allow suture material to be threaded through and tied across the bony bridge created by successive tunnels after it has been placed through the soft tissues and tied with conventional knots. Anchors fabricated from stainless steel or titanium are commonly used in joint reconstructions, and, because the metal is contained in the bone, it does not cause a problem with healing.

While endoscopy has certainly found favor with many physicians as an alternative operative modality, the advanced skill set and operative time necessary to become an efficient and practiced endoscopist have proven to be a challenge for a large portion of the surgical community. The cost pressures brought about by large scale patient management (the continued rise and success of health maintenance organizations or HMO's) have also caused the surgical community to cast a critical eye on the overall costs and long-term outcomes of some of the procedures that have been tried via an endoscopic approach. While the laparoscopic cholecystectomy (gall bladder removal) has certainly proven its worth in the past 8–10 years, many other procedures have not shown similar cost effectiveness and positive long-term outcomes.

Hence, alternatives have been sought to bridge the gap between the preferred endoscopic surgery, which is skill and equipment intensive, and the more familiar and easier open surgery, which is much more invasive and results in greater long-term discomfort and recovery time on the part of the patient. As such, under the broad umbrella of "minimally invasive surgery" which would include endoscopic surgery, a relatively new approach called "mini-incision surgery" has begun to emerge where the work area is view directly without an endoscope, but refined instruments are used to reach into a smaller opening. This approach uses the principles of traditional open surgery, along with some of the equipment advances of endoscopy to attempt to provide the patient with the best of both worlds.

Perhaps the most visible of these new approaches is the emergence of minimally invasive heart surgery, both for coronary bypass and for valve replacement. Techniques and tools for cardiovascular surgery have begun to be used that allow the heart surgeon to perform procedures through small incisions between the ribs that previously required a massive incision and splitting the sternum to gain access to the heart.

In a similar way, orthopedic surgeons have begun to explore alternatives to the traditional open approach for the many indications requiring reconstruction of some aspect of the shoulder. As they did in adopting minimally invasive approaches to knee repair and re-construction, the use of either an endoscopic or a "mini-open" approach is gaining in popularity with surgeons, patients and third party payers. However, a broad view of the various approaches to surgical procedures needs to weigh the patient benefits of endoscopic surgery (shorter hospital stay, less recovery time, less pain) against the costs of equipment and time to do the procedures.

It is an increasingly common problem for tendons and other soft, connective tissues to tear or to detach from associated bone. One such type of tear or detachment is a "rotator cuff" tear, causing pain and loss of ability to elevate and externally rotate the arm. Complete separation can occur if the shoulder is subjected to gross trauma, but typically, the tear begins as a small lesion that increases in size over time, especially in older patients.

The rotator cuff or a shoulder joint is made up of a combination of the distal tendinous portion of four muscles, supraspinatus and subspinatus, subscapularis and teres minor. The cuff is attached to the upper, anterior and posterior faces of the trochiter by covering the upper pole of the humeral head. Proper functioning of the tendinous cuff, 3 to 4 millimeters thick, depends on the fundamental centering and stabilizing role of the humeral head with respect to sliding action during anterior and lateral lifting and rotational movements of the arm.

The musculotendinous cuff passes under an osteofibrous arch, which is made up from the front to the rear by a portion of the acromion, the coracoacromial ligament and the coracoid process, thereby forming a canal. A sliding bursa passes between the musculotendinous cuff and the walls of the osteofibrous arch. Therefore, there is a potential and sometimes detrimental interaction between the musculotendinous cuff and the acromiocoracoidian arch, particularly during lateral and anterior lifting movements of the arm. The repeated rubbing of the cuff against the walls of the osteofibrous arch results in the wearing of the tendinous cuff by progressive abrasion. The rubbing can be increased inasmuch as arthrosis lesions with severe osteophytes may thicken the walls of the aforementioned arch, becoming more aggressive as the cuff gets older.

With time, gradual thinning is brought about, accompanied by a trophic perforation (less than 1 $cm^2$) of the cuff, particularly in the hypo-vascularized and fragile area where the supraspinatus muscle is joined. A fall may provide a more extensive rupture by disjunction of the supraspinatus muscle, with extension towards the front (subscapularis muscle) or the rear (subspinatus muscle). The degenerative rupture of the rotator or musculotendinous cuff may be of a varied size:

grade 1—perforation (less than 1 $cm^2$) reaching the supraspinatus muscle;

grade 2—supraspinatus rupture (greater than 1 $cm^2$);

grade 3—massive rupture concerning the supraspinatus, subspinatus, subscapularis muscles and sometimes the teres minor muscle.

It is possible to carry out surgery to reconstruct the rotator cuff. This is done by re-covering the humeral head with the supraspinatus tendon, giving back to the cuff its capturing and stabilizing role and re-establishing a harmonious scapulohumeral rhythm. Reconstruction most often requires excision of the coracoacromial ligament and cleaning the subacromial space, including suppression of the arthrosis legions and thinning of the anterior portion of the acromion in order to create a larger working area so the acromion doesn't impinge on the cuff during articulation of the arm.

The typical course for repair of a torn rotator cuff today is to do so through an open incision. This approach is presently taken in the vast majority of rotator cuff repair cases. Two types of open surgical approaches are known for repair of the rotator cuff, one of which is known as the "classic open" and the other as the "mini-open". The "classic open" approach typically requires a large incision of 6 to 9 centimeters (cm) and complete detachment of the deltoid muscle from the acromion to facilitate exposure. Following the suturing of the rotator cuff to the humeral head, the detached deltoid is surgically reattached. Because of this maneuver, the deltoid requires postoperative protection, thus retarding rehabilitation and possibly resulting in residual weakness. Complete rehabilitation takes approximately 9 to 12 months.

The "mini-open" technique, which represents the current growing trend and the majority of all surgical repair procedures, differs from the classic approach by gaining access through a smaller incision of 3 to 5 cm and splitting rather than detaching the deltoid. Additionally, this procedure is typically used in conjunction with arthroscopic acromial decompression. Once the deltoid is split, it is retracted to expose the rotator cuff tear. The cuff is debrided and trimmed to ensure suture attachment to viable tissue and to create a reasonable edge approximation. In addition, the humeral head is abraded or notched at the proposed soft tissue to bone reattachment point, as healing is enhanced on a raw bone surface. A series of small diameter holes, referred to as trans-osseous tunnels, are "punched" through the bone laterally from the proposed attachment point on the abraded or notched surface to a point on the outside surface of the greater tuberosity, commonly a distance of 2 to 3 cm.

There are a few different methods for placing the suture material in the supraspinatus tendon. Because one of the most common failure modes for rotator cuff repair lies in the sutures pulling out of the soft tissue, much care is taken to place the sutures such that the most security possible is achieved. This is typically done by using either a mattress stitch or a more complex stitch called a "modified Mason-Allen". The goal of both of these stitches is to spread the forces imparted by the sutures on the tissues by involving a pledget of tissue between the entry and exit points of the suture ends. The mattress stitch incorporates essentially a down, over and back up path for the suture.

Finally, the cuff is secured to the bone by pulling the suture ends through the trans-osseous tunnels and tying them together using the bone between two successive tunnels as a bridge, after which the deltoid muscle must be surgically reattached to the acromion.

Although the above described surgical technique is the current standard of care for rotator cuff repair, it is associated with a great deal of patient discomfort and a lengthy recovery time, ranging from at least four months to one year or more. It is the above described manipulation of the deltoid muscle together with the large skin incision that causes the majority of patient discomfort and an increased recovery time.

Less invasive arthroscopic techniques are beginning to be developed in an effort to address the shortcomings of open surgical repair. Working through small trocar portals that minimize disruption of the deltoid muscle, a few surgeons have been able to reattach the rotator cuff using various bone anchor and suture configurations. The rotator cuff is sutured intracorporeally using instruments and techniques such as the Caspari punch previously described. This creates a simple stitch instead of the more desirable mattress or Mason-Allen stitch. Rather than threading the suture through trans-osseous tunnels which are difficult or impossible to create arthroscopically using current techniques, an anchor is driven into bone at a location appropriate for repair. The repair is completed by tying the cuff down against bone using the anchor and suture.

Early results of less invasive techniques are encouraging, with a substantial reduction in both patient recovery time and discomfort. However, as mentioned supra, this approach is time consuming and complex and places only one loop of suture in the cuff for each anchor, reducing the fundamental strength of the repair. The knots in the tendon can be bulky and create a painful impingement of the tendon on the bone and have long term negative effects on the tendon. This is because the knots end up on top of the cuff, in the subacromial space, and have a tendency to rub on the acromion as the arm is raised. Because non-absorbable suture materials are used for these types of repairs, the suture and associated knots are not absorbed into the body, and hence provide a constant, painful reminder of their presence.

None of the prior art devices are adaptable to effect the placement of a mattress stitch in grasped tissues, nor are they adaptable to place sutures precisely and controllably while making provision for needle retrieval when using endoscopic techniques. None of the prior art devices make it possible to in a single step place a mattress stitch into, for example, the supraspinatus tendon utilizing an arthroscopic approach.

What is needed, therefore, is a family of novel suturing devices that overcome the above described disadvantages of prior known devices in a simple and economical manner. The devices should be capable of arthroscopically creating a mattress stitch in a tendon to increase the soft tissue pullout strength of the repaired tendon, or be able to place 2 independent single stitches without removing the device for side to side approximation of soft tissues.

SUMMARY OF THE INVENTION

Accordingly, the inventors have developed a new and novel approach for securing a mattress stitch in a tissue flap. An instrument that combines the function of both independently grasping the tissue and passing sutures through the tissue to form a mattress stitch is herein described.

More particularly, in one aspect of the invention there is provided a suturing device for use endoscopically, which comprises a clamping portion having a longitudinal axis, which is adapted for percutaneous entry into an operative site. The clamping portion further comprises a plurality of jaw members that are movable relative to one another between a closed position wherein the jaw members are disposed in close proximity to one another and an open position wherein the jaw members are spaced apart. A needle portion is disposed at an angle relative to the longitudinal axis, and is adapted for percutaneous entry into said operative site. The needle portion comprises a needle, and preferably a pair of needles, for passage through a portion of soft tissue disposed between the jaw members of the clamping portion.

Preferably, suturing material is disposed in one of the jaw members, and the needle is adapted for engaging the suturing material at the operative site. Each needle comprises a distal end which is configured for engaging the suturing material, which configuration is preferably a hook for gaffing the suturing material. The suturing material disposed in the one jaw member comprises a suture loop, and preferably two suture loops disposed on opposing sides of the one jaw member. The pair of needles each engage a respective one of the two suture loops.

The aforementioned needle portion preferably includes a needle guide having a pair of needle guide channels or tubes for guiding each of the pair of needles to the operative site. The guide tubes may be telescopically fixed to the needle portion to adjust for different patient dimensions.

In another aspect of the invention, there is provided a suturing device for use endoscopically, which comprises a clamping portion having a longitudinal axis, which is adapted for percutaneous entry into an operative site and which comprises a plurality of jaw members that are movable relative to one another between a closed position wherein the jaw members are disposed in close proximity to one another and an open position wherein the jaw members are spaced apart. One of the jaw members comprises first and second slots on opposing sides thereof, wherein a first looped end of a length of suturing material is disposed in the first slot and a second looped end of a length of suturing material is disposed in the second slot. The device further comprises a needle portion having first and second needles adapted for engagement with the first and second looped ends, respectively. In a preferred embodiment, the first and second needles are disposed at an angle relative to said longitudinal axis of between about 30 degrees and about 90 degrees.

In another aspect of the invention, there is provided a suturing device for use endoscopically, which comprises a tissue retaining portion having a longitudinal axis, which is adapted for percutaneous entry into an operative site through a cannula. The device further comprises a suture engagement portion spaced from the tissue retaining portion, which is adapted for percutaneous entry into the operative site through a location spaced from the cannula. Preferably, the tissue retaining portion comprises a clamping portion having means for retaining soft tissue which is to be attached to bone within the operative site. In a preferred embodiment, the retaining means comprises first and second jaw members which are movable relative to one another between a closed position, wherein the jaw members are disposed in close proximity to one another and an open position wherein the jaw members are spaced apart. Other equivalent structure, such as hooks, barbs, recesses, and the like, which are known in the art as being capable of retaining tissue in place, may also be utilized, and should be considered as being structurally equivalent to the described pair of jaws.

In still another aspect of the invention, there is disclosed a method of placing sutures in tissue, using a suturing device which comprises a clamping portion having a longitudinal axis and a needle portion spaced from the clamping portion. The inventive method comprises a step of inserting a distal end of the clamping portion percutaneously into an operative site until a distal working end thereof is adjacent to tissue which is to be repaired. The tissue is then engaged with the distal working end of the suturing device. A distal end of the needle portion is inserted percutaneously into the operative site, so that at least one needle of the needle portion extends through the engaged tissue and through a suture loop disposed on a distal side of the engaged tissue. Then, the at least one needle is withdrawn proximally to thereby pull the suture loop proximally through the engaged tissue to form a stitch through the tissue.

The invention, together with additional features and advantages thereof, may best be understood by reference to the following description taken in conjunction with the accompanying illustrative drawing.

DESCRIPTION OF THE PREFERRED EMBODIMENT

The present invention relates to a method and apparatus for the arthroscopic repair of torn tissue and bone at a surgical repair site using a device, which is a combination tissue grasper and suture placement device. Although the present invention is described primarily in conjunction with the repair of a torn rotator cuff, the apparatus and method could also be used in arthroscopic repair at other sites, such as the knee, elbow, or hip, for example, as well as in conjunction with other surgical techniques, such as traditional open or mini-open surgical procedures.

Figure 1:
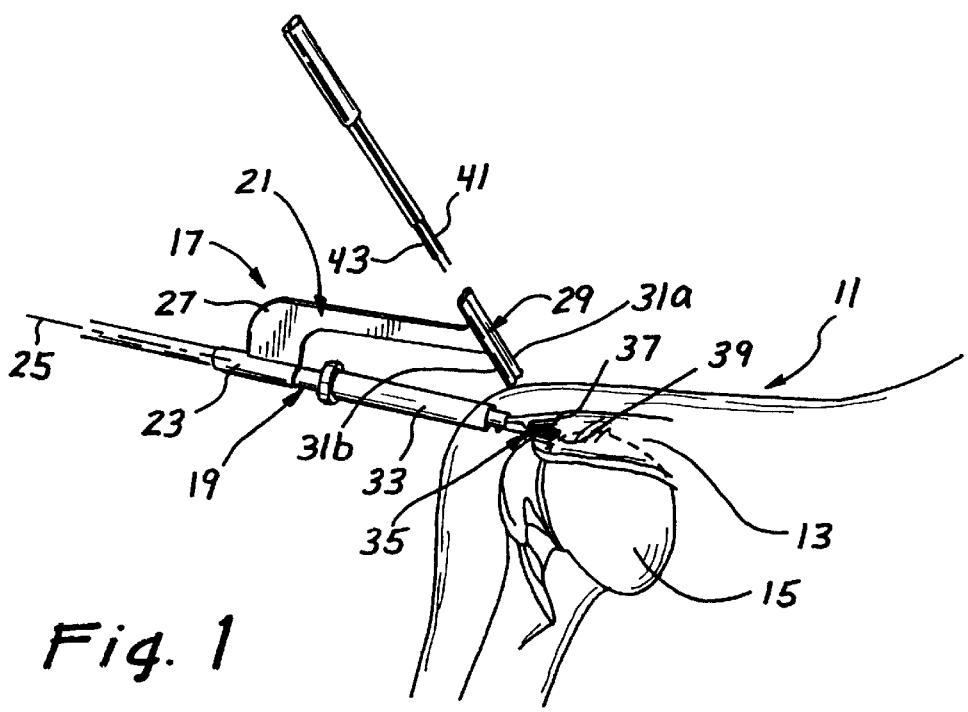
FIG. 1 is a schematic view illustrating a percutaneous suturing device constructed in accordance with the principles of the present invention, in a first operational position relative to a shoulder joint which is to be repaired.

Referring now to FIG. 1, there is shown a representative shoulder 11, including a torn rotator cuff 13, and a humeral head 15. As is common with rotator cuff injuries, in the illustrated example the torn rotator cuff 13 has pulled away from the head 15 of the humerus. A method of repair for such an injury which is a significant improvement over prior art approaches is discussed in co-pending U.S. patent application Ser. No. 09/876,488, entitled *Method and Apparatus for Attaching Connective Tissues to Bone Using a Knotless Suture Anchoring Device*, filed on Jun. 7, 2001, commonly assigned herewith, and expressly incorporated herein by reference.

According to the present invention, the objective is the same as in the '488 patent application, that being to re-attach the soft tissue (tendon) 13 to the humeral head 15, using a bone anchor to which has been secured suturing material which has also been sutured to the tendon 13. To accomplish this objective, a percutaneous suturing instrument 17 is placed in close proximity to the repair site, as shown in FIG. 1. The suturing instrument 17 comprises a clamping portion 19 and a needle portion 21. In a preferred embodiment, the instrument 17 further comprises a base portion 23. The clamping portion 19 extends axially in a distal direction from the base portion 23, along a longitudinal axis 25, and the needle portion 21 extends transversely from the base portion. The needle portion 21 includes a curved portion 27 for re-orienting the needle portion 21 so that it is substantially parallel to the clamping portion at a spaced distance therefrom, as shown in FIG. 1. Portions 19, 21, and 23 of the instrument 17 may be constructed of known relatively rigid structural materials suitable for medical instruments, such as plastic or metal, depending upon durability and cost parameters.

Figure 3:
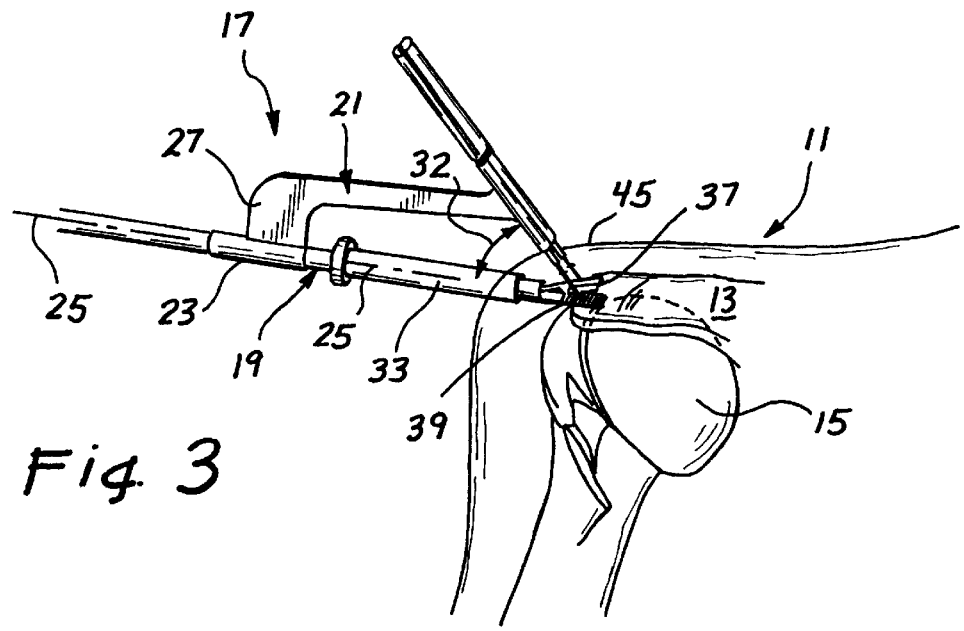
FIG. 3 is a schematic view similar to FIGS. 1 and 2, showing the needles of the inventive suturing device after they have penetrated the soft tissue to be repaired and engaged the suturing material.
Figure 4:
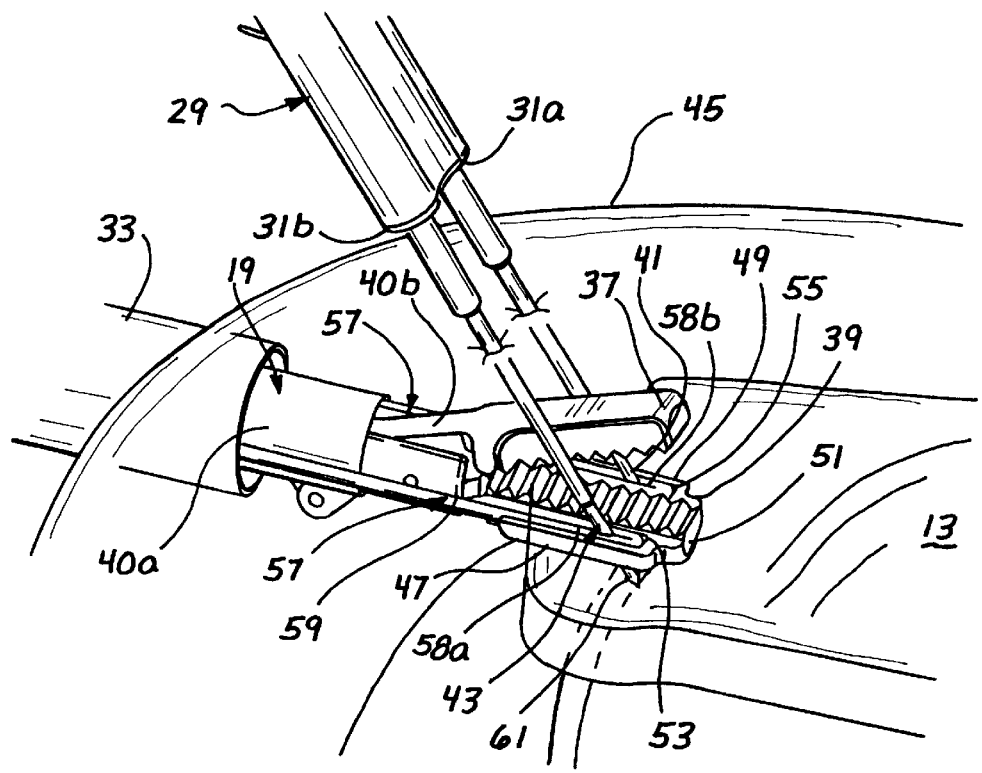
FIG. 4 is an enlarged schematic view showing the region in proximity to the distal end of the inventive device, with the needles thereof in the same position as shown in FIG. 3.

Disposed at a distal end of the needle portion 21 is a needle guide 29 which comprises a pair of needle guide channels 31a, 31b, as shown best in FIG. 4. Although a pair of needles is shown in these illustrations, it is to be understood that a single needle may be used to create a simple stitch. Multiple needles are used to create more complex suture constructs such as the mattress stitch, or to approximate the edges of a torn piece of tissue. An important feature of the invention is that the needle portion 21 is oriented to ensure that the needle guide, and thus the needles entering the patient's shoulder 11 therethrough, is at a desired angle relative to the clamping portion 19, thus ensuring a proper suturing procedure. Preferably, the needle guide 29 is oriented at an acute angle 32 relative to the longitudinal axis 25 of the instrument 17, as is shown in FIG. 3, for example. This acute angle, in preferred embodiments, is approximately 30–45 degrees, with 45 degrees being presently preferred, although the important feature is that the acute angle be substantially more than 0 degrees and less than 90 degrees. The reason for this is that it results in a suture angle 32a through the tissue 13 which is approximately the same as the angle 32 (see FIG. 6). By orienting the stitch 63 at such an angle 32a through the tissue 13, a great deal of stress on the tissue 13 is alleviated, thereby improving substantially the durability of the stitch and, thus, the chance for a successful outcome. Thus it may be seen that an angle of up to and even more than 90 degrees may be utilized, but is not preferred due to the additional stresses it places on the tissue 13.

It should be noted that the needle guide 29 and its associated guide tubes or channels 31a, 31b may be telescopically fixed to the needle portion 21, so that the position of the guide tubes may be adjusted for different patient dimensions.

A preferred method for utilizing the inventive apparatus 17 will now be described. Again with reference to FIG. 1, once the suturing instrument 17 has been placed in close proximity to the repair site, externally of the shoulder 11, the clamping portion 19 of the instrument is advanced distally through a trocar or cannula 33 which has been previously inserted into the shoulder 11 using known techniques. It is to be noted that the instrument 17 may alternatively be passed directly through an opening in the body without using a cannula 33. The distal clamping end 35 of the clamping portion 19 comprises a pair of jaws 37, 39 which are movable relative to one another to selectively closed and opened orientations, by means of a proximally disposed actuator (not shown). As seen best in FIGS. 4 and 5, the clamping portion 19 comprises, in part, a hollow barrel 40a, through which a linkage 40b forming a part of the actuator, is disposed. Any suitable actuator, such as a handpiece comprising a handle grip and a handle lever, with the handle lever being movable relative to the handle grip may be employed for such a purpose, wherein the linkage 40b connects the hand piece to the movable jaw. Once the jaws 37, 39 are fully inserted through the cannula 33 distally into the procedural site, they are manipulated, in their open position until they extend over the torn end of the soft tissue 13. At this point in time, the jaws are actuated to their closed orientation, thereby clamping the tissue 13, as shown in FIG. 1. Visualization of the procedural site is obtained by means of an endoscope or the like, which is inserted into a position in proximity to the procedural site through a second trocar cannula, not shown, although direct visualization may be used if performing, for instance, a mini open procedure.

Figure 2:
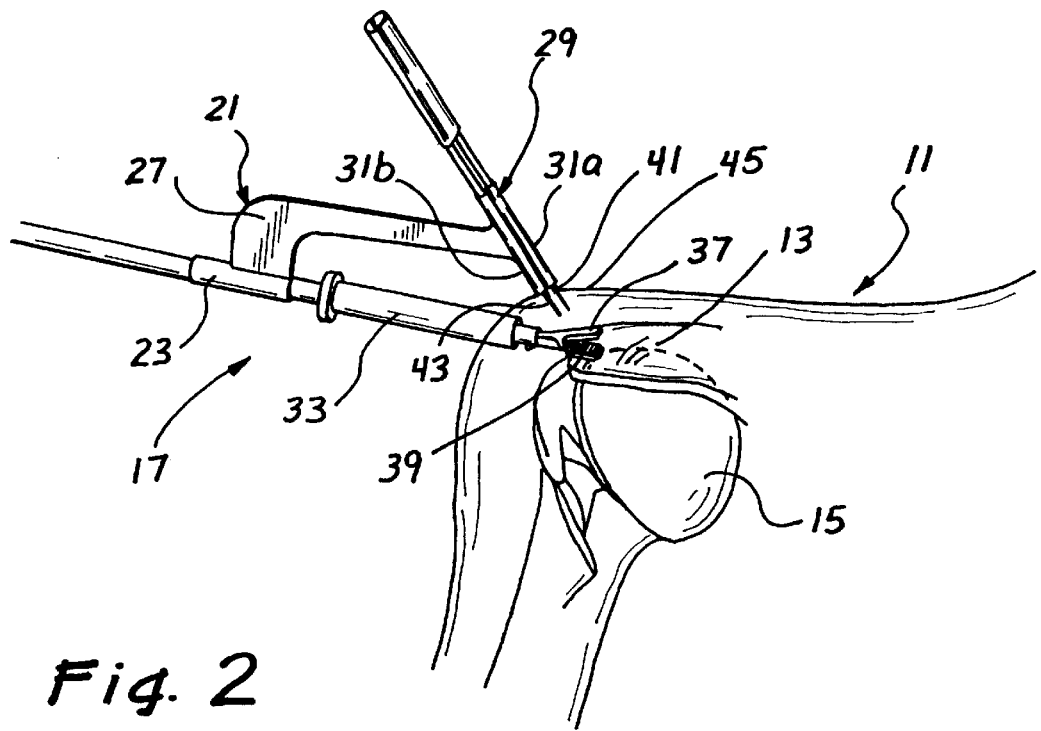
FIG. 2 is a schematic view similar to FIG. 1, illustrating the inventive suturing device after the needles of the device have penetrated the skin of the patient.

Referring now more particularly to FIG. 2, once the tissue 13 is clamped, a pair of needles 41, 43 are advanced distally through the needle guide channels 31a, 31b, respectively. Once they emerge from a distal end of the guide channels 31a, 31b, they continue to be advanced distally until they have penetrated the skin 45 of the shoulder 11.

Now with reference to FIGS. 3 and 4, it may be seen that the needles 41, 43, once they are beneath the skin 45, are further advanced distally past the upper jaw 37. It should be noted that although the lower jaw 39 is visible in FIGS. 3 and 4, this is for illustrative purposes only, as it would actually be obscured by the soft tissue 13 disposed between the two jaws 37, 39, as is seen in FIG. 5.

The lower jaw 39 preferably includes a pair of projecting members 47 and 49 extending from each side of the jaw 39, proximally from the distal end 51 of the jaw 39. Suture receiving slots 53 and 55 are defined by each of the projecting members 47 and 49, respectively. As shown in FIG. 4, suturing material 57 is disposed axially along either side of the clamping portion 19 of the instrument 17, extending along the slots 53 and 55. Although not shown, the two lengths of suturing material are joined together at the proximal end of the suturing instrument 17. In other words, the suturing material 57 is actually a single length of suture which is threaded, or "pre-loaded" through the instrument 17 in the manner shown or alongside the elongate body of the instrument 17. The suturing material 57 is preferably wrapped back upon itself to form a suture loop 58a, 58b within each of the slots 53 and 55, as shown. In one embodiment, a single-tailed braided suture of the type disclosed and described in co-pending, commonly assigned U.S. patent application Ser. No. 09/515,360, entitled *Single-Tailed Suturing Method and Apparatus*, filed on Feb. 29, 2000, and expressly incorporated herein by reference, is utilized as the suturing material 57. In this instance, the distal end of the suture 57 is looped back and inserted into the interior of the braided suture 57 at entry point 59, as shown. In alternative embodiments, the distal end of the suture 57 may be attached in some known fashion to the parallel length of suture, or the entire length of suture 57 may be doubled up. This doubling up of the suture increases the target area of suture that the needles 41 and 43 may penetrate, as described below. It is to be understood that the suture only needs to be held in place, not necessarily doubled, for the penetration to occur.

The needles 41, 43 each preferably include a hooked end or gaffe 61. As the needles 41, 43 are moved distally past the upper jaw 37, they pass through the slots 53 and 55, respectively, and thus also pass through or gaffe the suturing material 57 disposed in each slot 53, 55, as shown in FIGS. 3 and 4. Of course, the needles also pass through the soft tissue 13 in the process, protruding from beneath the lower jaw 39 as shown in FIG. 4.

Figure 5:
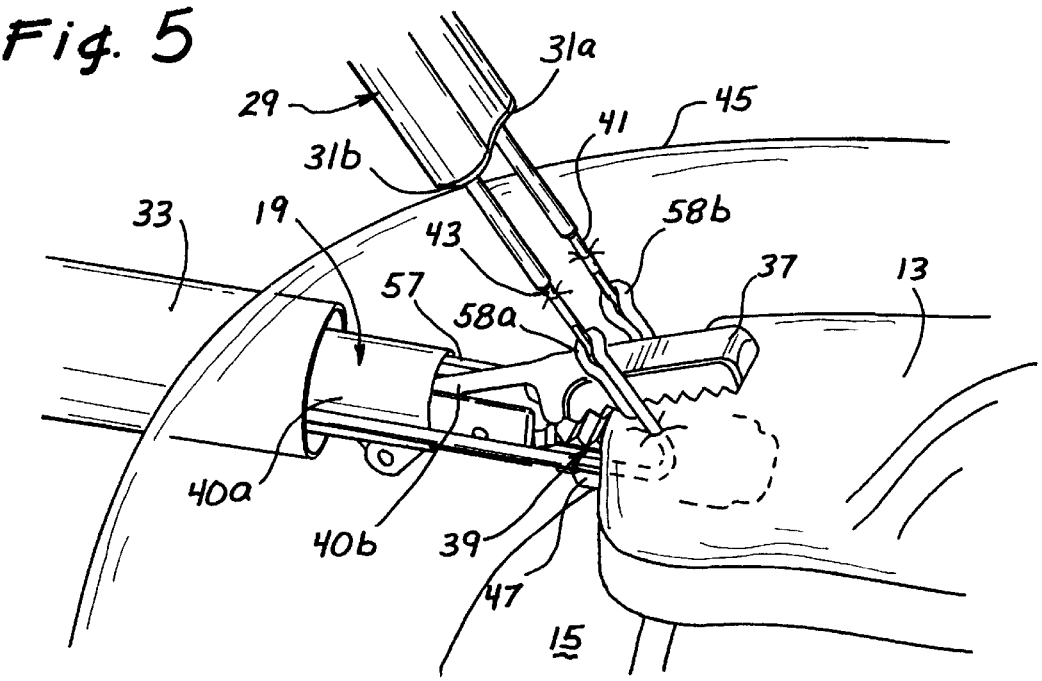
FIG. 5 is an enlarged schematic view similar to FIG. 4, showing the needles in a retracted position, having pulled the suturing material proximally out of the soft tissue.
Figure 6:
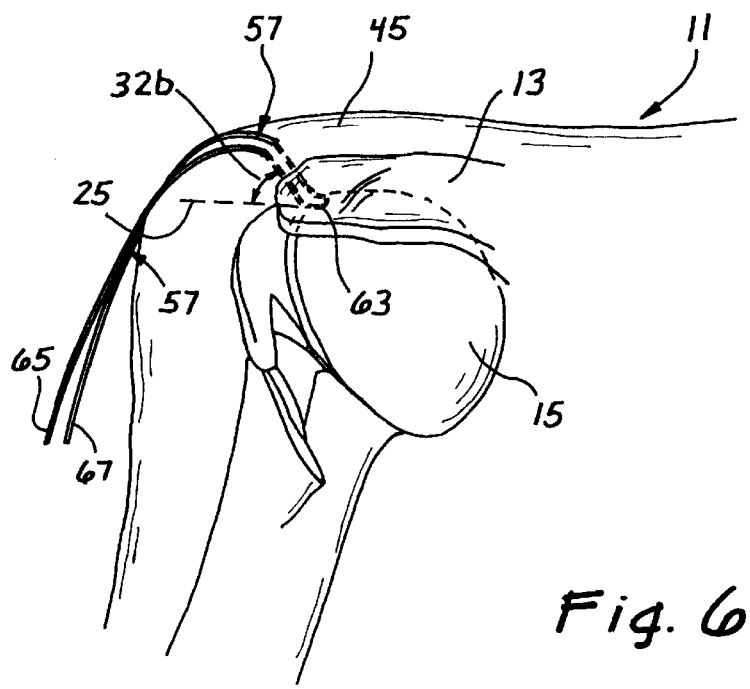
FIG. 6 is a schematic view of the shoulder after a first mattress stitch has been completed using the inventive suturing procedure, and the inventive suturing device has been withdrawn.

Referring now to FIG. 5, once the suture loops 58a and 58b are gaffed by the needles 41 and 43, respectively, the needles may be withdrawn proximally from the procedural site. As they are withdrawn, because of their engagement with the suture loops 58a and 58b, they will pull those suture loops proximally through the soft tissue 13, as shown in FIG. 5. Continued proximal travel of the suture loops 58a and 58b out of the patient's body, because of continued proximal travel of the needles 41 and 43, will cause the formation of a stitch 63, preferably a "mattress stitch", as shown in FIG. 6, within the soft tissue 13. At this juncture, the suturing material 57 may be disengaged from the needles 41, 43 by trimming the proximal loops 58a and 58b from the suturing material, or other suitable methods, creating merely trailing suture ends 65 and 67 extending from the shoulder 11.

Figure 7:
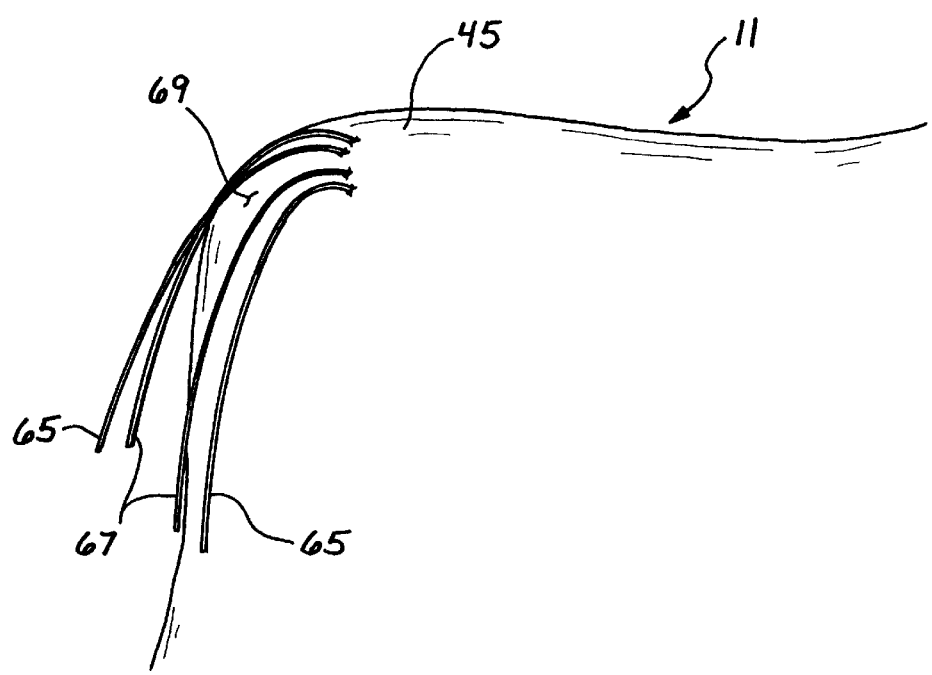
FIG. 7 is a schematic view of the external portion of the shoulder, after both first and second mattress stitches have been completed using the inventive suturing procedure.

FIG. 7 illustrates a case wherein, after the first stitch 63 is created, the entire procedure illustrated in FIGS. 1–6 is repeated to create a second stitch 63, and a second set of trailing suture ends 65, 67. The procedure may be repeated as many times as desired, to create a desired number of stitches 63 within the tendon 13, to ensure a successful repair. As a means of reference, the aperture through which the trocar or cannula 33 was placed during the above described procedure is shown and identified by reference numeral 69.

The apparatus and method of the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A suturing device for use endoscopically, comprising:
    a clamping portion having a longitudinal axis, which is adapted for percutaneous entry into an operative site and which comprises a plurality of jaw members that are movable relative to one another between a closed position wherein the jaw members are disposed in close proximity to one another and an open position wherein the jaw members are spaced apart and wherein at least one jaw member has and wherein at least one jaw member has at least one slot for receiving suturing material; and
    a needle portion disposed at an angle relative to said longitudinal axis, which is adapted for percutaneous entry into said operative site;
    said needle portion comprising a needle for passage through a portion of soft tissue disposed between the jaw members of said clamping portion;
    wherein said clamping portion and said needle portion enter the operative site through different percutaneous locations.

2. The suturing device as recited in claim 1, and further comprising suturing material disposed in one of said jaw members, said needle being adapted for engaging said suturing material at said operative site.

3. The suturing device as recited in claim 2, wherein said needle comprises a distal end which is configured for engaging said suturing material.

4. The suturing device as recited in claim 3, wherein said distal end is hooked for gaffing said suturing material.

5. The suturing device as recited in claim 2, wherein the suturing material disposed in the one jaw member comprises a suture loop.

6. The suturing device as recited in claim 5, wherein there are two suture loops disposed on opposing sides of said one jaw member.

7. The suturing device as recited in claim 5, and further comprising a second needle, each of said needles engaging a respective one of said two suture loops.

8. The suturing device as recited in claim 1, wherein said angle is between about 30 and about 90 degrees.

9. The suturing device as recited in claim 1, wherein said needle portion includes a needle guide having a needle guide channel for guiding said needle to the operative site.

10. The suturing device as recited in claim 9, wherein the needle guide is telescopically fixed to the needle portion to adjust for different patient dimensions.

11. A suturing device for use endoscopically, comprising:
    a clamping portion having a longitudinal axis, which is adapted for percutaneous entry into an operative site and which comprises a plurality of jaw members that are movable relative to one another between a closed position wherein the jaw members are disposed in close proximity to one another and an open position wherein the jaw members are spaced apart and wherein at least one jaw member has at least one slot for for receiving susturing material at least one slot for receiving suturing material, and
    a needle portion disposed at an angle relative to said longitudinal axis, which is adapted for percutaneous entry into said operative site;
    said needle portion comprising a needle for passage through a portion of soft tissue disposed between the jaw members of said clamping portion, and further including a needle guide having a needle guide channel for guiding said needle to the operative site;
    wherein the needle guide is telescopically fixed to the needle portion to adjust for different patient dimensions.

12. The suturing device as recited in claim 11, wherein said clamping portion and said needle portion enter the operative site through different percutaneous locations.

13. The suturing device as recited in claim 11, and further comprising suturing material disposed in one of said jaw members, said needle being adapted for engaging said suturing material at said operative site.

14. The suturing device as recited in claim 13, wherein said needle comprises a distal end which is configured for engaging said suturing material.

15. The suturing device as recited in claim 14, wherein said distal end is hooked for gaffing said suturing material.

16. The suturing device as recited in claim 13, wherein the suturing material disposed in the one jaw member comprises a suture loop.

17. The suturing device as recited in claim 16, wherein there are two suture loops disposed on opposing sides of said one jaw member.

18. The suturing device as recited in claim 16, and further comprising a second needle, each of said needles engaging a respective one of said two suture loops.

19. The suturing device as recited in claim 11, wherein said angle is between about 30 and about 90 degrees.

* * * * *

UNITED STATES PATENT AND TRADEMARK OFFICE
CERTIFICATE OF CORRECTION

PATENT NO. : 6,605,096 B1
DATED : August 12, 2003
INVENTOR(S) : Ritchart

It is certified that error appears in the above-identified patent and that said Letters Patent is hereby corrected as shown below:

Column 12,
Line 4, after "has" delete "and wherein at least one jaw member has".
Line 54, after "has" delete "and at least one slot for receiving susturing material".

Signed and Sealed this

Fifteenth Day of March, 2005

JON W. DUDAS
*Director of the United States Patent and Trademark Office*